United States Patent [19]

Beck

[11] 4,260,812

[45] Apr. 7, 1981

[54] PROCESS FOR THE PREPARATION OF HALOGEN BUTENYL ACRYLATES

[75] Inventor: Manfred Beck, Odenthal, Fed. Rep. of Germany

[73] Assignee: Bayer Aktiengesellschaft, Leverkusen, Fed. Rep. of Germany

[21] Appl. No.: 49,073

[22] Filed: Jun. 18, 1979

[30] Foreign Application Priority Data

Jun. 22, 1978 [DE] Fed. Rep. of Germany ....... 2827323

[51] Int. Cl.³ ............................................. C07C 67/10
[52] U.S. Cl. .................................................. 560/223
[58] Field of Search ................ 560/223, 225, 237, 111

[56] References Cited

U.S. PATENT DOCUMENTS

| | | | |
|---|---|---|---|
| 3,255,163 | 6/1966 | Gobran et al. ........................ | 560/223 |
| 3,634,474 | 1/1972 | Hay et al. ............................. | 560/237 |
| 3,879,445 | 4/1975 | Gray et al. ............................ | 560/111 |

FOREIGN PATENT DOCUMENTS 2038954  2/1971  Fed. Rep. of Germany ........... 260/237

*Primary Examiner*—Natalie Trousof
*Assistant Examiner*—L. Hendriksen
*Attorney, Agent, or Firm*—Connolly and Hutz

[57] ABSTRACT

Halogenbutenylacrylates of formula

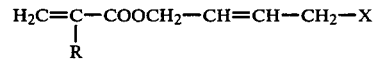

in which R represents hydrogen or $C_1$–$C_4$ alkyl and X represents halogen may be produced by reacting an acrylic acid salt of formula

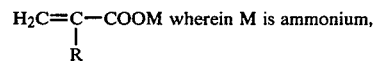

wherein M is ammonium, alkali metal or alkaline earth ion, with 1,4-di-halogen-butene-(2) in a diphasic system.

8 Claims, No Drawings

PROCESS FOR THE PREPARATION OF HALOGEN BUTENYL ACRYLATES

This invention relates to a one-step process for the preparation of halogen butenyl acrylates by the reaction of substituted or unsubstituted acrylic acid salts with 1,4-di-halogen-butene-(2) in a diphasic system.

A process for the preparation of halogen butenyl acrylates has been disclosed in U.S. Pat. No. 3,255,163. The compound is obtained by subjecting acrylic acid esters to a transesterification reaction in the presence of 4-halogen-2-butenols. This process requires a large excess of acrylic acid esters which may only be worked-up with difficulty and considerable loss. Moreover, 4-halogen-2-butenol-(1) which is used as starting material may only be prepared by a multi-stage synthesis which also entails considerable loss. The process described is therefore technically disadvantageous.

A reaction of dibromo-alkenyls with potassium acetate to form the corresponding bis-acetates has been published in Synthesis 1974, page 867, but the preparation of the corresponding mono-compounds has not been described. References are not made to the reaction of unsaturated carboxylic acids with dihalogen alkenyls to form mono-substitution products. The process described requires large quantities of a phase transfer catalyst, i.e. 22 mol percent, based on the halogen alkyl, so that the reaction may hardly be referred to as a catalysis.

Both halogen atoms of 1,4-dihalogenbutene-2are highly reactive. The raid hydrolysis may be mentioned as an example. When 1,4-dichlorobutene-2is reacted with sodium carbonate at 100° C., only a mixture of two isomeric butene diols is isolated (Pudovik, Ž. Obsč. Chim. 19 (1949) 1185, CA 1950, 1005).

On the basis of the ease of hydrolysis of both halogen atoms in 1,4-dichlorobutene-2 which has thereby been demonstrated, one would have expected the preparation of the corresponding chlorobutenyl esters in an alkaline/neutral aqueous medium to be accompanied by a hydrolysis to 4-hydroxy-butenyl ester. It is surprisingly found that this reaction does not occur.

It has now been found that acrylic acid esters of 4-halogen-2butenol-(2) are obtainable by a one-step process of reacting substituted or unsubstituted acrylic acids with 1,4-dihalogen butene-(2). The process is carried out in a diphasic system. The aqueous phase contains an alkali metal or alkaline earth metal salt of acrylic acid and the organic phase consists of the dihalogen butene used in excess, optionally diluted with a solvent.

The reaction may be accelerated by means of a phase transfer catalyst selected from quaternary ammonium, phosphonium or sulphonium salts. it takes place in accordance with the following reaction scheme:

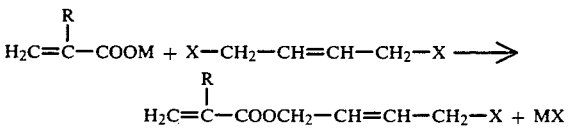

wherein
R represents H or C$_1$-C$_4$-Alkyl
X represents halogen as Cl, Br or I; and
M represents an ammonium, an alkali metal or alkaline earth metal (bearing in mind the valency of the metal ion).

The present invention thus relates to a process for the preparation of halogen butenyl acrylates corresponding to the following general formula (I):

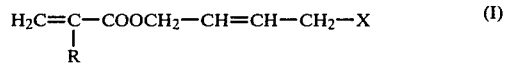

wherein
R represents hydrogen or a C$_1$-C$_4$ alkyl groups; and
X represents a halogen atom; which process is characterised in that a salt of acrylic acid corresponding to the following general formula (II):

wherein
R represents hydrogen or a C$_1$-C$_4$ alkyl group; and
Me represents an ammonium, an alkali metal or alkaline earth metal ion;
is reacted with 1,4-dihalogen butene-(2) in proportions of 1 mol of the acrylic acid salt to from 1 to 7 mols of the dihalogen butene in a diphasic system at temperatures of from 10° to 140° C.

Examples of suitable alkyl substituents R include: methyl, ethyl, propyl, isopropyl, butyl, isobutyl and tertiary butyl. Methyl is preferred.

The halogen substituent X may be chlorine, bromine or iodine. Chlorine is preferred.

The solvent optionally used for the dihalogen butene may be a water-immiscible solvent, preferably an aliphatic or aromatic hydrocarbon such as hexane, cyclohexane, toluene or xylene.

The alkali metal and/or alkaline earth metal may be sodium, potassium, magnesium, calcium, strontium or barium. Sodium and potassium are particularly preferred.

The reaction of acrylic acid with dihalogen butene is preferably carried out using an excess of from 2 to 5 mols of 1,4-dihalogen butene per mol of acrylic acid. This method has the advantage that it may be carried out in the absence of solvent if desired. The process of working-up is easier in this preferred method. The two phases are separated from each other after the reaction and the organic phase is fractionated. This fractionation is particularly easy since excess dichlorobutene may easily be removed in a first column owing to its relatively low boiling point. The ester is obtained in a high degree of purity as a side stream in a second column. It is obtained in yields of from 60 to 78%, based on the acid put into the process, and from 70 to 80%, based on dichlorobutene. The excess dichlorobutene is completely recovered.

The present process has the advantage over the known process that it may be carried out using inexpensive dilute acrylic acid as obtained from commercial processes. Moreover, it does not require an excess of this compound. Unreacted acrylic acid may be recovered from the aqueous phase.

The reaction is generally carried out by heating a stirred diphasic mixture of the salt of acrylic acid dissolved in water and the halogen compound. In addition to the phase transfer catalyst, one or more known polymerisation inhibitors or stabilizers may be added to the mixture, for example hydroquinone, N-nitrosodiphenylamine, p-t-butylpyrocatechol, 4-methoxy phenol, phenothiazine or mixtures thereof. The reaction is preferably carried out at temperatures of from 60° to 100° C., most preferably from 80° to 95° C.

Quaternary ammonium, phosphonium and sulphonium compounds are suitable for use as the phase transfer catalysts which may be used. Generally, the general formula thereof is as follows:

RR'R''R'''E+X− wherein

R, R' and R''' each represent an optionally hydroxy substituted aliphatic or aromatic group;

E represents a nitrogen or phosphorus atom; and

X represents an anion.

Generally, the general formula of the sulphonium compounds is as follows:

RR'R''S+X−, the various definitions being as above.

Ammonium compounds are preferably used, for example the following:
tetrabutyl ammonium halides,
tetraoctyl ammonium halides,
octyl-tributyl ammonium halides,
octadecyl tributyl ammonium halides,
octyl-bis(hydroxyethyl)-benzyl ammonium halides,
dodecyl-bis(hydroxypropyl)-benzyl ammonium halides and
octadecyl-dimethyl-benzyl ammonium halides.

The catalyst is generally used in a quantity of from 0.01 to 10 mol percent. Quantities of from 0.1 to 5.0 mol percent, particularly from 0.2 to 1.0 mol percent, are preferred.

The unsaturated esters which may be prepared by the process are valuable comonomers for polymerisations started by radical initiation. The simplicity of the process renders them available on a large technical scale for the first time. Owing to the reactivity of the γ-chlorine atom, they are suitable for the preparation of γ-amino- or γ-acyloxy- substituted acrylic acid esters.

EXAMPLE 1

A solution of the sodium salt of methacrylic acid is prepared from 191.3 g of methacrylic acid (90%;2 mol), 331.5 g of water and 175.2 g of 50 weight % sodium hydroxide solution (2.2 mol), with the addition of 2.5 g of N-nitrosodiphenylamine, 2.5 g of 4-methoxyphenol and 8 g of $(C_{12-18}H_{29-37})$ N$^{\oplus}$(CH$_2$CHOHCH$_3$)$_2$-CH$_2$C$_6$H$_5$)Cl$^{\ominus}$(70%) and the solution is heated to 90° C. 750 g (6 mol) of 1,4-dichlorobutene-2 are then added, with stirring, over a period of 10 minutes. After heating at the same temperature for 1 hour, 8 g of NaOH (50%) are added and the mixture is left to react for a further 2 hours. It is then cooled and stirring is stopped. After separation of the phases, the lower, aqueous phase is removed and the organic phase is distilled under vacuum, using a packed column (height 30 cm). The first fraction, which is separated at from 25 to 58° C. (2.3 mb), consists of 530 g of dichlorobutene (4.24 mol). The second fraction (Bp from 72° to 80° C./2 mb). contains pure 4-chloro-2-butenyl methacrylate. 242,2 g (69.4% of the theoretical yield, ≙ 1.39 mol) are isolated. 44.9 g of a low viscosity substance is left as residue. On the basis of thin layer chromatography, this still contains from 20 to 30% of the ester. The distilled chlorobutenyl ester is stabilized using 50 ppm of 4-methoxyphenol.

$n_D^{25}$=1.4808.

Analysis: Calculated: C 55.02; H 6.35; Cl 20.31; O 18.32.

$C_8H_{11}ClO_2$ obtained: C 55.0; H 6.5; Cl 20.3; (174.63); O 18.6.

EXAMPLE 2

Chlorobutenyl methacrylic acid ester is prepared by a method analogous to that of Example 1, but using only 4 mol (500 g) of 1,4-dichlorobutene-2. After working-up of the reaction product as in Example 1, 208.5 g of the ester (59.6% of the theoretical amount) are obtained and 275 g of dichlorobutene (2.2 mol) are recovered.

EXAMPLE 3

The reaction is carried out analogously to Example 1, but using 8 mol of 1,4-dichlorobutene-2 (1,000 g). Working-up of the reaction product yields 271.4 g (77.7% of the theoretical yield of the ester.

EXAMPLE 4

A solution of the sodium salt of methacrylic acid is prepared from 95.65 g (1 mol) of methacrylic acid (90%) 87.6 g (50%) of NaOH and 165.8 g of water. 1.2 g of N-nitrosodiphenylamine and 1.2 g of 4-methoxyphenol are added and 250 g (2 mol) of 1,4-dichlorobutene-2 are rapidly run in, with stirring, at 90° C. 4 g of a 50% sodium hydroxide solution are added after 1 hour and the reaction mixture is then heated, with stirring, for a further 2 hours. The phases are then separated. 0.72 mol of NaCl is found in the aqueous phase by the argentometric method. The organic phase is distilled as described above. 169.0 g (135 mol) of dichlorobutene and 67.5 g of 4-chlorbutenyl-methacrylate, corresponding to 38.5% of the theoretical yield, are obtained. The butene diol dimethyl acrylate is contained in the residue of low viscosity (6.8 g).

Much lower yields are therefore obtained without catalyst.

EXAMPLE 5

An aqueous solution of sodium acrylate is prepared from 216.2 g of acrylic acid (100%=3 mol), 262.8 g of NaOH (50%) and 497 g of water. 3.7 g of N-nitrosodiphenylamine and 3.7 g of 4-methoxyphenol are added to stabilize the solution. 12 g of the quaternary ammonium salt used in Example 1 are also added. 1,125 g (9 mol) of 1,4-dichlorobutene are run in at 90° C. 15.9 g of Na$_2$CO$_3$ are added after 1 hour and the mixture is left to react for a further 2 hours at 90° C. After phase separation, the organic layer is distilled under vacuum. 286.0 g (1.78 mol) of 4-chloro-2-butenyl acrylate (59.4% of the theoretical yield) are obtained. 641 g (5.13 mol) of dichlorobutene are recovered.

I claim:

1. In the process for the preparation of halogen butenyl acrylates corresponding to the formula $$H_2C=\underset{R}{C}-COOCH_2-CH=CH-CH_2-X$$

wherein

R represents hydrogen or a C$_1$-C$_4$ alkyl group; and

X represents a halogen atom;

wherein the improvement comprises reacting in an aqueous organic diphasic system at 10° to 140° C. a salt of acrylic acid of the formula

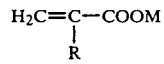

wherein M is ammonium, alkali metal or alkaline earth metal, with 1,4-dihalogen butene-(2) in proportions of 1 mol of acrylic acid salt to from 1 to 7 mol of the dihalogen butene.

2. Process according to claim 1, characterised in that the reaction temperature is from 60° to 100° C.

3. Process according to claim 2, characterised in that the reaction temperature is from 80° to 95° C.

4. Process according to claim 1 characterised in that from 2 to 5 mol of 1,4-dihalogen butene-(2) are used per mol of a salt of acrylic acid corresponding to general formula (II).

5. Process according to claim 1 characterised in that the reaction is carried out in the presence of a phase transfer catalyst selected from quaternary ammonium, phosphonium and sulphonium salts.

6. Process according to claim 5 characterised in that the phase transfer catalyst is used in quantities of from 0.01 to 10 mol percent of total reactants.

7. Process according to claim 6 characterised in that the phase transfer catalyst is present in quantities of from 0,1 to 5 mol percent of total reactants.

8. Process according to claim 5, characterised in that the phase transfer catalyst is present in quantities of from 0.2 to 1 mol percent of total reactants.

* * * * *